United States Patent [19]

Chakrabarti et al.

[11] 4,259,474

[45] * Mar. 31, 1981

[54] SULFUR-CONTAINING POLYOXYALKYLENES

[75] Inventors: Paritosh M. Chakrabarti, Wayne; Lindley S. Wood, Montclair; David J. Tracy, Lincoln Park, all of N.J.

[73] Assignee: GAF Corporation, New York, N.Y.

[*] Notice: The portion of the term of this patent subsequent to Mar. 10, 1998, has been disclaimed.

[21] Appl. No.: 78,708

[22] Filed: Sep. 25, 1979

[51] Int. Cl.³ .............................................. C08G 75/14
[52] U.S. Cl. ........................................ 528/388; 427/389; 427/393.1; 428/411; 428/413; 428/480; 428/532; 525/403; 525/404; 525/409; 528/381; 528/419; 528/421; 548/151; 548/251; 260/DIG. 15; 260/DIG. 17; 260/DIG. 19; 568/49; 568/62
[58] Field of Search ............... 260/DIG. 15, DIG. 17, 260/DIG. 19, 609 R, 609 F; 528/381, 388, 419, 421; 525/403, 404, 409; 427/390 B, 389; 428/411, 413, 480, 532; 548/157, 251

[56] References Cited

U.S. PATENT DOCUMENTS 3,936,422  2/1976  Wirth et al. .................. 260/45.95 N
3,988,378  10/1976  Wirth et al. ...................... 260/609 F Primary Examiner—Melvyn I. Marquis Attorney, Agent, or Firm—James Magee, Jr.; Marilyn J. Maue

[57] ABSTRACT

The sulfur-containing polyoxyalkylenes having the formula:

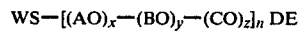

wherein E is —SW or a halogen atom; W is hydrogen, phenyl, alkyl of 1 to 4 carbon atoms, an alkali metal or ammonium ion, or a heterocyclic radical containing from 2 to 4 hetero atoms in a 5-or 6-membered ring which may be monocyclic or may be fused to an aromatic ring; A, C and D represent lower alkylene of 2 to 4 carbon atoms; B is alkylene of 2 to 8 carbon atoms; y and z are each integers having a value of 0 to 50; x is an integer having a value of from 2 to 50; and n is an integer having a value of from 1 to 30; and intermixtures of said polyoxyalkylenes.

The above compounds display a wide variety of uses; however, all are active metal working lubricants. Additional fields of utility, which may vary in the degree of activity for the various members of the above group include liquid dispersants, emulsifiers, low foaming surfactants for paints, pigments and dyes, anti-static agents, mold release agents, heat transfer fluids and anti-oxidants.

21 Claims, No Drawings

SULFUR-CONTAINING POLYOXYALKYLENES

The products of the present invention can be desirable anti-static agents since they may be incorporated as monomers in the homo- or co-polymerization of hydrophobic monomers in the synthesis of artificial fibers. The present compounds can also be used to impregnate yarns, filaments and woven or knitted fabrics made from such fibers as those of acrylonitrile/vinylchloride copolymers, e.g. Dynel; cellulose triacetate, e.g. Arnel; terephthalic acid/ethylene glycol copolymers, e.g. Dacron; polyacrylonitrile, e.g. Orlon; polyamine/carboxylic acid condensation products, e.g. Nylons; polyethylene; polypropylene and other hydrophobic polyesters, polyamides, polyacrylonitriles and polyalkylenes as well as their mixtures and/or blends with natural fibers, such as cotton, wool and rayon.

While such synthetic fibers and materials have many advantages properties, they have comparatively low capacity to retain moisture thus, accumulating electrostatic charges when subjected to normal friction as encountered in fabric processing or in wearing garments made of such fibers. The charged fibers also have the undesireable tendency to attract lint and soil and to give off spark discharges which, under certain circumstances, may constitute a serious hazard.

The same electrostatic charge build-up exists in commercial processing tanks and piping which is fabricated of such nonmetallic material having low electrical conductivity or where resins of such materials are used for lining tanks which cannot be effectively grounded. These fabricating and lining materials used in industry include molded polystyrene, polyvinylchloride, polyvinyl acetate, phenol/formaldehyde plastics, melamine glass cloth, Teflon coatings, polychlorotrifluoroethylene, Plexiglass molded articles and others discussed on pages 99 to 102 of Chemical Engineering, June 1, 1959.

Thus, it is highly desirable to modify these polymers so as to dissipate the static charges by increasing their electrical conductance to a specific area conductivity higher than $10^{-12}$ reciprocal ohm. Many hydrophilic chemicals have been proposed for incorporation with the hydrophobic materials, such as the disulfates, dihalides and polyamines of polyoxyethylene, as disclosed in British Pat. No. 797,175. However, these chemicals have a tendency to yellow and lack the degree of fabric penetration and affinity to withstand laundering. Other hydrophilic additives have a tendency to foam and form discontinuous films on a substrate. Also many such hydrophilic polymers are solid at room temperature and have little compatability with hydrocarbon substrates, while still others are thermally unstable at temperatures above which are frequently encountered in pressurized dyeing.

Accordingly, it is an object of this invention to overcome the above disadvantages and to provide economical sulfur-containing polyoxyalkylenes having a wide variety of uses.

Another object of this invention is to provide improved anti-static agents suitable for increasing the electrical conductivity of hydrophobic fabrics and formed plastics while exhibiting excellent high temperature stability and resistance to yellowing.

Still another object of the invention is to provide economical and efficient wetting agents and emulsifiers.

Another object is to provide oxidation inhibiting dispersants for dyes, pigments and paints.

Still another object is to provide improved lubricants and mold release agents.

These and other objects and advantages of the present invention will become apparent from the following description and disclosure.

According to this invention, there is provided new and useful sulfur-containing polyoxyalkylenes having the formula:

$$WS-[(AO)_x-(BO)_y-(CO)_z]_n-DE \quad \text{I.}$$

wherein E is —SW or a halogen atom such as a iodine, chlorine or bromine atom; W is hydrogen, phenyl, alkyl of 1 to 4 carbon atoms, an alkali metal or ammonium ion, or a heterocyclic radical containing from 2 to 4 hetero atoms in a 5- or 6-membered ring which may be monocyclic or may be fused to a aromatic ring; A, C and D represent lower alkylene of 2 to 4 carbon atoms; B is alkylene of 2 to 8 carbon atoms; y and z are each integers having a value of 0 to 50; x is an integer having a value of from 2 to 50; and n is an integer having a value of from 1 to 30; and intermixtures of said polyoxyalkylenes. Of these compounds, (a) those wherein x, y and z taken together, average 7 to 60, E is —SW, n is 1, A and D are the same and are ethylene or isopropylene and W is an inorganic radical, or (b) those wherein each of x, y and z are 20 to 50, E is —SW, n is 2 to 30, A and D are the same and are ethylene or isopropylene, and W is an inorganic radical, are preferred. Of this preferred group, those most desirable are the compounds wherein y and z are 0; and x is an integer between 7 and 25. However, it is to be understood that the value of x, y and z, as well as the radicals A, B, C and D in the above compounds and their mixtures, can be varied considerably in accordance with the needs of the particular application in which the product is to be employed.

Examples of sulfur-containing polyoxyalkylenes within the preferred group of compounds include those having the formulae:

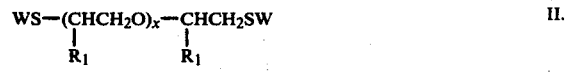

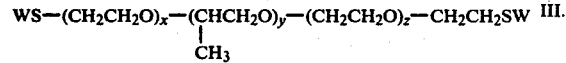

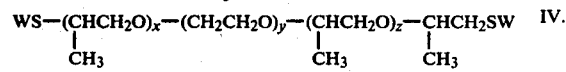

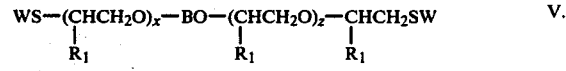

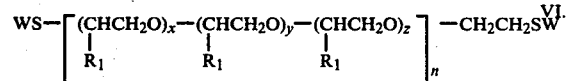

where in each of formulae II, V and VI, $R_1$ is hydrogen or methyl and B is formula V is alkylene of 4 to 8 carbon atoms; x in formula II is an integer having a value of 2 to 25; x and z in formulae III, IV and V are integers having a value of 2 to 20; y in formulae III and IV is an integer having a value of 1 to 20; and x, y and z in formula VI are each independently, e.g. 20 to 50 and n is 2 to 30. Also, within this preferred group are mixtures of the above, where E is —SW containing a minor amount of the corresponding mixture where E is a halogen atom.

When it is desirable to polymerize a compound of the present invention with another monomer, it is recommended that W in the above formula, represent a replaceable hydrogen in order that polymerization can easily be initiated. Also, it is desirable that the compound be of relatively low molecular weight for better compatability with the comonomer. However, when the present compounds are to be employed as thickeners, a high molecular weight species is frequently recommended. Generally, a polymer having at least 8 of the above-defined polyoxyalkylene units is preferred. Although it is to be understood that individual compounds within the scope of Formula I can be isolated by liquid chromatography, or by any other convenient method, the products of the present invention are usually employed as mixtures wherein at least x, or x and y of the individual components in the mixture, may have different values. Such mixtures are also contemplated wherein A, B and/or C represent different alkylene groups, as well. These mixtures have significantly higher boiling points and are more compatable with hydrocarbon chemicals than the individual polymers. The mixtures also provide superior antioxidants for cosmetics, polyalkylene glycol based lubricants and petroleum based lubricants, such as hydrocarbon hydraulic fludis. The polymeric mixtures are also usefully employed as solvents, plasticizers and suspension or dispersion agents for hydrocarbon systems. In petroleum systems, the present mixtures also possess detergent properties, e.g. for motor oils.

Examples of heterocyclic radicals represented by W in Formula I include, the radicals of thiazoline, thiazole, benzoxazole, benzothiazole, benzimidazole and tetrazole.

In general, the compounds of the present invention are economical to prepare since most are derived from readily available starting materials. The preparation of the present compounds involves the reaction of a sulfur compound with the dihalide derivative of a polyoxyalkylene having the structure:

halogen-$[(AO)_x$—$(BO)_y$—$(CO)_z]_n$-D-halogen    VII.

wherein A, B, C and D, as well as x, y, z and n are as defined above in Formula I and the halogen atoms are chlorine, iodine or bromine. The sulfur compound which reacts with the above dihalide is selected from the group of an alkali metal thiol; ammonium thiol; an alkali metal salt or ammonium salt of an alkyl mecercaptan of 1 to 4 carbon atoms or of phenyl- mercaptan; mercapto thiazoline; mercapto thiazole; 2-mercapto benzothiazole; mercapto benzothiazine; 2-mercaptodiazoline mercapto thiodiazoles; thiotriazoles; N-phenyl-2-mercaptotetrazole, which heterocyclics may be optionally substituted with methyl or phenyl on a heterocyclic nitrogen; and an alkali metal sulfide or an ammonium sulfide.

The preferred mole ratio of polyoxyalkylene dihalide to sulfur-containing reactant is as close to the stoichiometric ratio as is convenient to maintain depending on whether a mono-substituted of di-substituted product is desired. Generally, when a monochloride product is desired as the major product of the process, a mole ratio of polymeric dihalide to sulfur-containing reactant between about 1:0.06 and about 1:1.6 is satisfactory. However, when it is desirable to replace both terminal halogen atoms in the polymeric species with the sulfur-containing radical, a mole ratio of polymeric dihalide to sulfur-containing reactant between about 1:1.8 and about 1:2.5 can be employed.

The present invention is carried out in an inert atmosphere in the presence of an organic solvent. Suitable solvents are those inert organic solvents having a boiling point above the reaction temperature. Typical solvents of this type include toluene, xylene, naphthalene, chlorobenzene, cyclohexanol, decanol, octanol, dimethylformamide, N-methylpyrrolidone, hexamethylphosphoramide and pyrrolidone. The concentration of solvent in the system can be generally between about 35 and about 80 weight %, preferably between about 40 and about 60 weight %, based on the reactants in the reaction zone.

The present reaction is effected at a temperature of between about 70° C. and about 175° C., under from about 10 to about 50 psi, and is completed in a period of from about 4 to about 20 hours; preferably the reaction is carried out between about 90° C. and about 135° C., under from atmospheric to about 20 psi, and is completed within 8 to about 17 hours, depending upon the degree of conversion desired and the molecular weight of the polymeric reactant. The degree of conversion can be readily determined by measuring the amount of alkali haide formed, e.g. by argiometric titration. Although the reaction can be carried out in an open or a closed system, closed system operation reduces oxidative side reactions and results in shorter reaction time and better temperature control. The nonhalogenated product mixtures, or nonhalogenated and monohalogenated products, of the present process can be obtained in a yield and purity of up to 98%, after removal of the solvent, which can be easily separated by distillation or any other convenient method. Alkali metal halide or ammonium halide by-product can be separated by filtration.

The polyoxyalkylene dihalides and their intermixtures in the present invention are readily obtained by several methods, for example, they may be obtained by reacting the corresponding polyalkylene glycols with a molar excess of thionyl halide at moderate temperatures, e.g. between about 20° C. and about 125° C. under atmospheric pressure for a period of at least about 10 hours. The reaction is described in more detail in Belgian Pat. No. 554,506 filed Jan. 25, 1957 and a general discussion of the glycols is presented in Kirk-Othmer's Encyclopedia of Chemical Technology second edition, volume 10, page 659.

The polymeric glycols of the same or mixed monomers are also readily obtainable. For example, such glycols are commercially available as PLURONIC ® Polyols supplied by Wyandotte Chemicals Corporation and are listed in following Table I. Of these Pluronic Polyols, P104, F108, L43, 25R2, 25R8 and F127 are particularly suitable.

TABLE I

| | SUITABLE PLURONIC POLYOLS | | | |
|---|---|---|---|---|
| Form* | Pluronic Grade | Average Molecular Weight | Flash Point, (COC) °F. | Refractive Index 25° C. |
| L | 10R5 | 1970 | >450 | 1.4587 |
| F | 10R8 | 5000 | >450 | — |
| L | 17R1 | 1950 | >450 | 1.4516 |
| L | 17R2 | 2100 | >450 | 1.4535 |
| L | 17R4 | 2700 | >450 | 1.4572 |
| F | 17R8 | 7500 | >450 | — |
| L | 25R1 | 2800 | >450 | 1.4521 |
| L | 25R2 | 3120 | >450 | 1.4541 |

TABLE I-continued
SUITABLE PLURONIC POLYOLS

| Form* | Pluronic Grade | Average Molecular Weight | Flash Point, (COC) °F. | Refractive Index 25° C. |
|---|---|---|---|---|
| L | 25R4 | 3800 | >450 | 1.4574 |
| P | 25R5 | 4500 | >450 | — |
| F | 25R8 | 9000 | >450 | — |
| L | 31R1 | 3200 | >450 | 1.4522 |
| L | 31R2 | 3400 | >450 | 1.4542 |
| P | 31R4 | 4300 | — | — |
|  | L31 | 1100 | 37 | — |
|  | L35 | 1900 | 77 | — |
|  | F38 | 5000 | >100 | 45 |
|  | L42 | 1630 | 37 | — |
|  | L43 | 1850 | 42 | — |
|  | L44 | 2200 | 65 | — |
|  | L61 | 2000 | 24 | — |
|  | L62 | 2500 | 32 | — |
|  | L62LF | 2450 | 28 | — |
|  | L62D | 2450 | 35 | — |
|  | L63 | 2650 | 34 | — |
|  | L64 | 2900 | 58 | — |
|  | P65 | 3500 | 82 | 29.5 |
|  | F68 | 8350 | >100 | 50 |
|  | F68LF | 7700 | 32 | 47 |
|  | L72 | 2850 | 25 | — |
|  | P75 | 4150 | 82 | 34 |
|  | F77 | 6500 | >100 | 48 |
|  | L81 | 2750 | 20 | — |
|  | P84 | 4200 | 74 | 34 |
|  | P85 | 4600 | 85 | 40 |
|  | P87 | 7850 | >100 | 49 |
|  | F88 | 10,800 | >100 | 55 |
|  | F92 | 3500 | 26 | — |
|  | P94 | 4600 | 76 | 38 |
|  | F98 | 13,500 | >100 | 56 |
|  | L101 | 3800 | 15 | — |
|  | P103 | 4900 | 86 | 30 |
|  | P104 | 5800 | 81 | 37.5 |
|  | P105 | 6350 | 91 | 42 |
|  | F108 | 15,500 | >100 | 57 |
|  | L121 | 4500 | 14 | — |
|  | L122 | 4900 | 19 | — |
|  | F123 | 5650 | 90 | — |
|  | P127 | 11,500 | >100 | 56 |

L—Liquid
P—Paste
F—Flakeable Solid
> = greater than

Many processes are known for the preparation of the glycols, e.g. the Encyclopedia of Chemical Technology, second edition, by Kirk-Othmer, Volume 10, pages 654-659. Also as one of several alternatives, the preparation of the glycols can be effected by the dehydration of

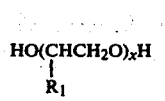

and the alkylene glycol corresponding to $-(BO)_y-$; for example:

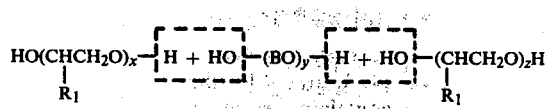

A more conventional procedure involves the polymerization of propyleneoxide monomer with polyoxyethylene or vice versa, under basic conditions. The glycol is then converted to the corresponding halide as described herein or by any other known process for preparing the polyoxyalkylene halide reactants of this invention.

As stated above, the sulfur-containing polymeric products of the present invention are useful as additives in many fields of application. Generally, their use as additives to formulations, such as paint vehicles, polymerization media, dye baths, cosmetic creams, oil or water based lubricants, etc. involves utilization of the present compounds in a wide range of concentrations, e.g. from as little as about 0.05% to about 20% by weight, preferably from about 0.1% to about 15% by weight based on the formulation. However, as a modifier in a polymerization reaction, the concentration of the present sulfur-containing product may extend up to 50% by weight, based on the total monomer mixture.

Having generally described the invention, reference is now had to the accompanying examples which illustrate preferred embodiments but which are not to be construed as limited to the scope of the invention as set forth above and as defined in the accompanying claims. All amounts and proportions recited in the following examples are by weight, unless otherwise indicated.

EXAMPLE 1

Into a glass round bottom flask, equipped with a mechanical stirrer, a heating mantle, and a thermometer, which is maintained under an inert atmosphere, is added 118 grams of sodium thiol as a 40% aqueous solution and 166 grams of a polyoxyethylene dichloride mixture having the formula:

wherein the averaged value of x is 18. The temperature is then raised to initiate reaction at 100°-110° and the reaction mixture is maintained with constant stirring at atmospheric pressure for 12 hours.

After 12 hours, 41.8 grams of sodium chloride by-product is formed, indicating a conversion of about 94% of the dichloride mixture to the corresponding mixture of dithiols, heating is discontinued, the sodium chloride is removed by filtration, the reactor is allowed to cool, and 154 grams of the corresponding dithiol polymeric mixture having the formula:

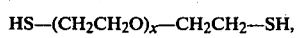

wherein x has an averaged value of 8, is collected as a light yellow liquid mixture having a S analysis of 14.3%, (Theory=14.8%).

The correspondingly dithiol substituted polymeric oxyalkylene mixture is obtained in the same yield and purity when other polyoxyethylene dihalides or polyoxypropylene dihalides e.g. where x is 10, 12 or 21, as in the dihalides of P1000, P1200 and P2000, are substituted for the polyoxyethylene dichloride employed in this example.

EXAMPLE 2

The above example is repeated except that only 59 grams of sodium thiol as a 40% aqueous solution are added to the reactor and the reaction is terminated after 9 hours when, at 110°-120° C., 22 grams of sodium chloride by-product is formed. The product removed from the reactor is a mixture of mono- and di- thiolated polyoxyethylenes having the formulae:

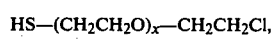

and $$HS-(CH_2CH_2O)_x-CH_2CH_2SH$$

wherein x has an averaged value of 8. The products, in 94% yield and 98% purity, are separated and recovered. The thiol polyoxyethylene monochloride mixture has a S analysis of 7.24%. The correspondingly monothiol substituted polyoxyalkylene mixture is obtained in the same yield and purity when other polyoxyethylene dihalides or polypropylene dihalides e.g. where x is 12 or 21, as in the dihalides of P1200 and P2000, are substituted for the polyoxyethylene dichloride in this example.

EXAMPLE 3

Into a glass round bottom flask, equipped as in Example 1, is added 24.7 grams of potassium sulfide, $K_2S$, as a 55% aqueous solution and 118 grams of a polyoxyalkylene dichloride mixture having the formula:

$$Cl(CH_2CH_2O)_x-(CHCH_2O)_y-(CH_2CH_2O)_z-CH_2CH_2Cl$$
$$|$$
$$CH_3$$

wherein the averaged value of x+z in the mixture is 12 and the averaged value of y in the mixture is 10. The temperature is raised to 125° C. and is maintained with constant stirring for a period of 15 hours, after which heating is discontinued, the mixture is allowed to cool to room temperature and potassium chloride by-product is separated and solvent is removed by distillation. The recovered product, which is the corresponding product mixture having the formula:

$$KS(CH_2CH_2O)_x-(CHCH_2O)_y-(CH_2CH_2O)_z-CH_2CH_2SK$$
$$|$$
$$CH_3$$

is obtained in about 90% yield and 95% purity. The % S is 4.76%.

EXAMPLE 4

The procedure reported in Example 3 above is repeated, except that 167 grams of a polyoxyalkylene dichloride mixture having the formula:

$$Cl(CHCH_2O)_x-(CH_2CH_2O)_y-(CHCH_2O)_z-CHCH_2Cl$$
$$|\qquad\qquad\qquad |\qquad\qquad |$$
$$CH_3\qquad\qquad\qquad CH_3\qquad\qquad CH_3$$

wherein the average of x+z in the mixture is 20 and wherein the average of y in the mixture is 10, is substituted for the polyoxyalkylene dichloride employed in Example 3. Similarly, 166 grams of a corresponding dithiol product mixture having the formula:

$$KS(CHCH_2O)_x-(CH_2CH_2O)_y-(CHCH_2O)_z-CHCH_2SK$$
$$|\qquad\qquad\qquad |\qquad\qquad |$$
$$CH_3\qquad\qquad\qquad CH_3\qquad\qquad CH_3$$

wherein x, y and z are as defined above in this example, is recovered from the flask as a heavy light yellow viscous liquid in about 95% yield and about 92% purity. The % S is 3.30%.

EXAMPLE 5

Example 3 is repeated except that 120 grams of a polyoxyalkylene dichloride mixture having the formula:

$$Cl(CH_2CH_2O)_x-CH_2CH_2CH_2CH_2O-(CH_2CH_2O)_z-CH_2CH_2Cl$$

wherein the average of x+z in the mixture is 24, is substituted for the polyoxyalkylene dichloride mixture and $Na_2S$ is substituted for aqueous $K_2S$ of Example 3. Similarly, 109 grams of a corresponding dithiol polymeric mixture having the formula:

$$NaS(CH_2CH_2O)_x-CH_2CH_2CH_2CH_2O-(CH_2CH_2O)_z-CH_2CH_2SNa$$

where x and z are as defined above in this example is recovered as a heavy light yellow viscous liquid in greater than 87% yield and about 90% purity. The % S is 4.6%.

EXAMPLE 6

Into a glass round bottom flask equipped with a mechanical stirrer, container 150 ml of xylene is added 150 grams of anhydrous sodium thiophenoxide. To the resulting mixture is introduced 666 grams of a polyoxypropylene dichloride mixture (P2000 dichloride), having the formula:

$$Cl(CHCH_2O)_x-CHCH_2Cl$$
$$|\qquad\qquad\qquad |$$
$$CH_3\qquad\qquad CH_3$$

wherein x has an averaged value of 21. The flask is heated to 100° C. for 20 hours during which the reaction mixture is constantly stirred. The mixture is then gradually cooled to 15°–20° C. over a period of 2 hours, after which xylene is removed by distillation from the corresponding product mixture of oxypropylene sulfide polymer, having the formula:

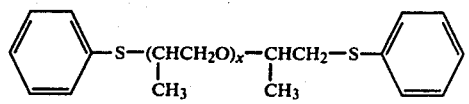

where x has an averaged value of 21. The product is recovered in 80% yield and 90% purity. The sulfur analysis is 3.90%.

EXAMPLES 7 THROUGH 11

The following examples are generally carried out as set forth in Example 1, except for the operating conditions and sulfur-containing reactant reported in the following table. As in Example 1, these reactions are carried out under atmospheric pressure and in an inert atmosphere. In the following, toluene or chlorobenzene is used as the solvent. The % Conversions to the corresponding non-chlorinated product mixtures are as reported below.

TABLE I

| EX. # | AMOUNT (gms) OF S-CONTG. REACTANT | REACTION TEMP./ TIME (°C./HRS.) | % CONVERSION/% PURITY DISUBSTITUTED PRODUCT | % PRODUCT FOR USES OTHER THAN ANTISTATIC AGENTS |
|---|---|---|---|---|
| 7. | 66g. of $Na_2S$ | 100–120° C./18 | 94/91 | 10–50% for copolymerization |
| 8 | 168g. of $K_2S$ (55% aqueous) | 125° C./15 | 94/95 | 10–50% for copolymerization |
| 9. | 190g of $(NH_4)_2S$ (30% aqueous) | 100–120° C./18 | 90/87 | 10–50% for copolymerization |
| 10. | 43g. of $NH_4SH$ | 100–120° C./18 | 91/90 | 10–50% for copolymerization |
| 11. | 156g. of NaS—C 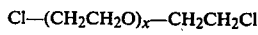 | 140–150° C./18 | 95/99 | 2–5% coupling agent, dye modifier |

EXAMPLE 12

Into a 1 gal. jacketed stainless steel kettle equipped with a mechanical stirrer is added 515 grams of 2-mercaptobenzothiazole and 655 grams of a polyoxyethylene dichloride mixture (based on UCON-400) having the formula:

$$Cl-(CH_2CH_2O)_x-CH_2CH_2Cl$$

wherein the averaged value of x is 8. Agitation is begun and 1240 grams of 10% caustic soda is added over a period of 1 hour. The kettle is then evacuated and the mixture heated to 100°–110° C. for 8 hours with constant agitation. The product:

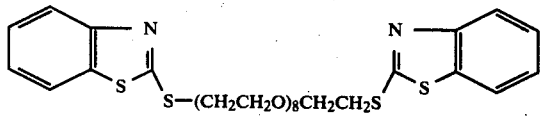

is recovered by extraction with $CH_2Cl_2$ and, after treatment with charcoal, is isolated as a yellow liquid in 85% yield (%S=17.3%).

EXAMPLE 13

Into a 1 gallon jacketed stainless steel kettle equipped with a mechanical stirrer is added 365 gm of 1-phenyl-2-mercaptotetrazole and 1,150 grams of a polyoxyalkylene dichloride mixture having the formula:

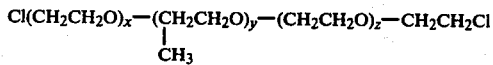

wherein the averaged value of x+z in the mixture is 11 and the averaged value of y in the mixture is 10. The slurry is heated to 35°–40° C. with agitation and 160 grams of 50% caustic soda added over a period of 1 hour. The kettle is then evacuated and the mixture heated to 110°–115° C. with agitation for a period of 15 hours. The water is removed by distillation and salt removal facilitated by digestion in methanol. Removal of the methanol provides 90% pure product having the formula:

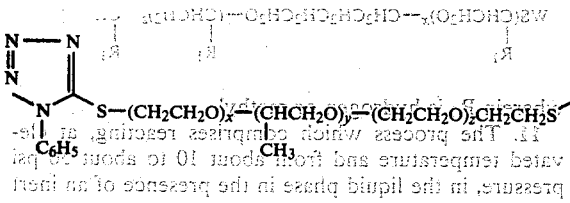

recovered in 94% yield (%S=4.1%).

EXAMPLE 14

Into a glass round bottom flask equipped with a mechanical stirrer, is added 450 grams of butyl mercaptan and 400 grams of 50% caustic soda. To the resulting mixture is introduced 1,093 grams of a polyoxyethylene dichloride mixture (PEG 400 dichloride), having the formula:

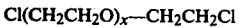

wherein x has an averaged value of 8. The flask is heated and held at 100° C. for 22 hours during which the reaction mixture is constantly stirred. The mixture is then cooled to 15°–20° C. gradually over a period of 2 hours, after which sodium chloride precipitate is filtered and water and organic volatiles are distilled from the corresponding product mixture of oxyethylene sulfide polymer, having the formula:

$$C_4H_9S-(CH_2CH_2O)_x-CH_2CH_2-SC_4H_9$$

where x has an averaged value of 8. The product is recovered in 97% yield and 85% purity. The sulfur analysis is 10.0%.

EXAMPLE 15

Into a glass round bottom flask equipped with a mechanical stirrer, containing 150 ml of xylene is added 110 grams of a 30% aqueous solution of the sodium salt of methylthiol. To the resulting mixture is introduced 450 grams of a polyoxyethylene dibromide mixture (PEG 2000 dibromide), having the formula:

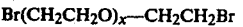

wherein x has an averaged value of 21. The flask is then sealed, heated to 100° C. and the contents stirred for 20 hours. The mixture is then gradually cooled to 15°–20° C. over a period of 2 hours, after which sodium bromide is filtered and the xylene and water are distilled from the corresponding product mixture of oxyethylene sulfide polymer, having the formula:

$$H_3CS-(CH_2CH_2O)_x-CH_2CH_2-SCH_3$$

where x has an averaged value of 21. The product is recovered in 90% yield and 95% purity. The sulfur analysis is 3.0%.

EXAMPLE 16

The products of Examples 1 through 15 are each dissolved in methylene chloride or water to provide 2% solutions. A 1.5×11.5 inch strip of Dacron 56 Taffeta is immersed in each of the solutions for approximately 10 minutes. The impregnated strip is then removed and air dried without curing and tested for electrostatic build-up. Each of the impregnated strips is stroked 50 times against a polyvinylchloride fabric surface and then placed on top of an ashtray containing cigarette ashes. There is no ash pick-up on the strip which indicates substantially complete discharge of static electricity.

The above results are repeated when strips of Nylon, Orlon or Arnel are substituted for Dacron in this example.

EXAMPLE 17

Aqueous solutions of each of the products of Examples 1 through 7 (5 grams/liter) are made up in seven glass flasks. Acrylonitrile monomer is added with stirring to each of the aqueous solutions and a stable emulsion formed upon addition. Polymerization is initiated at 55° C. in the presence of 0.3 gram potassium persulfate catalyst. The polymerization reaction is effected at 60°–70° C. without any agglomeration of the polymerizing particles and polyacrylonitrile is recovered as a particulate solid.

EXAMPLE 18

The product of Example 3 and the product of Example 5 are separately added to one of two one quart cans of outdoor white latex paint to provide 2% mixtures therein and the mixtures stirred for two hours. The resulting paint mixtures are noticeably thickened and the paint of each quart showed an improved affinity for the surfaces painted and superior resistance to oxidative or photochemical degradation. Additionally, the surface tension of the paint is increased resulting in less foaming than the untreated paint on application.

It is to be understood that other sulfur-containing products made from other polyoxyalkylene mixtures wherein the average of x, y and/or z is, for example 10, 12, 16, 24 or higher and wherein the polymeric dihalide contains at least two different monomeric units, such as for example wherein A, C and D are ethylene and B is isopropylene or wherein A, C and D are isopropylene and B is ethylene or wherein C is omitted and A and D are isopropylene and B is ethylene or wherein C is omitted and A and D are ethylene and B is isopropylene or any of the above mixtures for A and D or A, C and D where B is butylene, penthylene, hexylene, heptylene or octylene and many other combinations which are apparent from the foregoing description and disclosure, can be substituted in Examples 17 through 18 to give good results.

What we claim is:

1. A sulfur-containing polyoxyalkylene product having the formula:

wherein E is halogen or —SW; W is hydrogen, phenyl, alkyl of 1 to 4 carbon atoms, an alkali metal or ammonium ion, or a heterocyclic radical containing 2 to 4 hetero atoms in a 5- or 6-membered ring which is monocyclic or may be fused to an aromatic ring; A, C and D represent lower alkylene of 2 to 4 carbon atoms; B is alkylene of 2 to 8 carbon atoms; y and z are each integers having a value of from 0 to 50, x is an integer having a value of from 2 to 50; n is an integer having a value of from 1 to 30.

2. The product of claim 1 wherein said product is a mixture of said sulfur-containing compounds; x, y and z taken together have an average value of 7 to 60; A and D are the same and are ethylene or isopropylene, E is —SW and W is an inorganic radical.

3. The product of claim 2 wherein y and z are zero and x is an integer having a value between about 7 and 25.

4. The product of claim 3 having the formula:

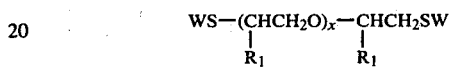

where W is sodium or potassium and $R_1$ is hydrogen or methyl.

5. The product of claim 3 having the formula:

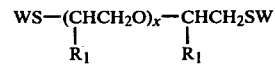

where W is a 5-membered heteromonocyclic ring and $R_1$ is hydrogen or methyl.

6. The product of claim 3 having the formula:

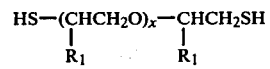

where $R_1$ is hydrogen or methyl.

7. The product of claim 3 having the formula:

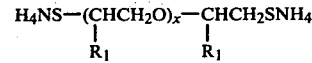

wherein $R_1$ is hydrogen or methyl.

8. The product mixture of claim 1 wherein a major portion of the mixture comprises compounds where E is SW and a minor portion of the mixture comprises compounds where E is halogen.

9. The product of claim 2 having the formula:

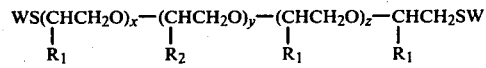

wherein $R_1$ and $R_2$ are each hydrogen or methyl and $R_2$ is other than $R_1$.

10. The product of claim 2 having the formula:

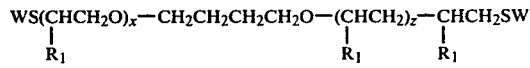

wherein $R_1$ is hydrogen or methyl.

11. The process which comprises reacting, at elevated temperature and from about 10 to about 50 psi pressure, in the liquid phase in the presence of an inert solvent, a sulfur-containing compound selected from the group of an alkali metal salt or an ammonium salt of an alkyl mercaptan of 1 to 4 carbon atoms or of phenyl mercaptan; ammonium thiol; an alkali metal thiol; a heterocyclic mercaptan containing from 2 to 4 hetero atoms in a 5- or 6-membered ring which is monocyclic or may be fused to a phenyl or a naphthyl ring; and the sulfide of an alkali metal or ammonium, with at least one polymeric compound having the formula:

$$\text{halo-}[(AO)_x-(BO)_y-(CO)_z]_n-\text{D-halo}$$

wherein halo is an iodine, chlorine or bromine atom; A, C and D represent lower alkylene of 2 to 4 carbon atoms; B is alkylene of 2 to 8 carbon atoms; y and z each represent integers having a value from 0 to 50 and x represents an integer having a value of from 2 to 50; n is 1 to 30; to produce the product of claim 1.

12. The process of claim 11 wherein the sulfur-containing compound is a sulfide and the reaction is carried out in the presence of between about 35 and about 60 weight % of an inert organic solvent.

13. The process of claim 11 wherein about 35 and 60 weight % of an aqueous solvent is employed.

14. The process of claim 11 wherein the mole ratio of sulfur-containing compound to polymeric dihalide is between about 0.6:1 and about 1.5:1 and a monothiolated product is obtained.

15. The process of claim 11 wherein the mole ratio of sulfur-containing compound to polymeric dihalide is between about 1.7:1 and about 2.5:1 and a dithiolated product is obtained.

16. The process of claim 15 wherein the polymeric dihalide reactant is a mixture having the formula:

$$\text{halo}-(AO)_x\text{D}-\text{halo}$$

wherein A and D are lower alkylene of 2 to 4 carbon atoms and halo is an iodine, chlorine or bromine atom and x has an averaged value of 7 to 25 is reacted with a sulfur-containing compound of the group ammonium thiol, an alkali metal thiol, ammonium sulfide or an alkali metal sulfide at a temperature of between about 90° C. and about 135° C.

17. The process of claim 11 wherein the polymeric reactant is a mixture having the formula:

$$\underset{R_1}{Cl(CHCH_2O)_x}-(BO)_y-\underset{R_1}{(CHCH_2O)_z}-\underset{R_1}{CHCH_2Cl}$$

wherein $R_1$ is hydrogen or methyl, B is ethylene, isopropylene or butylene and (BO) is different from any other monomeric unit in the polymer, x and z are each integers from 7 to 20 and y is an integer from 1 to 20, is reacted with ammonium thiol, an alkali metal thiol, ammonium sulfide or an alkali metal sulfide at a temperature of between about 90° C. and about 135° C.

18. The process of incorporating between about 0.05 and about 50 weight % of the product of claim 1 in a hydrophobic substance.

19. The process of incorporating between about 1.5 and about 30 parts by weight of the product of claim 2 in 100 parts by weight of a hydrophobic fabric to provide antistatic properties therein.

20. The process of introducing between about 0.05 to about 20% by weight of the product of claim 1 to a polymerization mixture containing a hydrophobic monomer.

21. The process of incorporating between about 2 and about 30 weight % of at least one of the products of claim 10 in a hydrophobic substance.

* * * * *

UNITED STATES PATENT AND TRADEMARK OFFICE
CERTIFICATE OF CORRECTION

PATENT NO. : 4,259,474

DATED : March 31, 1981

INVENTOR(S) : Paritosh M. Chakrabarti, Lindley S. Wood & David J. Tracy

It is certified that error appears in the above—identified patent and that said Letters Patent is hereby corrected as shown below:

In "Table I-continued" at column 5, lines 1-44:

"> 450" should be inserted on line 11, 4th column as on the stapled sheet...

a line should be drawn under said line 11 and the last two columns should be captioned "Cloud Point °C. *" and "Melting Point °C." respectively, as shown on the stapled sheet...

the last two polyols in Table I, lines 38 and 39, should read "P123" and "F127" respectively, as shown on the stapled sheet; and in the legend at the bottom of the table "*in 1% aqueous solution" should be inserted, as shown.

Signed and Sealed this

Twenty-third Day of February 1982

[SEAL]

Attest:

GERALD J. MOSSINGHOFF

Attesting Officer

Commissioner of Patents and Trademarks

TABLE I-continued
SUITABLE PLURONIC POLYOLS

| Form* | Pluronic Grade | Average Molecular Weight | Flash Point, (COC) °F. | Refractive Index 25° C. |
|---|---|---|---|---|
| L | 25R4 | 3800 | >450 | 1.4574 |
| P | 25R5 | 4500 | >450 | — |
| F | 25R8 | 9000 | >450 | — |
| L | 31R1 | 3200 | >450 | 1.4522 |
| L | 31R2 | 3400 | >450 | 1.4542 |
| P | 31R4 | 4300 | >450 | — |

| | Average Molecular Weight | Cloud Point °C. * | Melting Point °C. |
|---|---|---|---|
| L31 | 1100 | 37 | — |
| L35 | 1900 | 77 | — |
| F38 | 5000 | >100 | 45 |
| L42 | 1630 | 37 | — |
| L43 | 1850 | 42 | — |
| L44 | 2200 | 65 | — |
| L61 | 2000 | 24 | — |
| L62 | 2500 | 32 | — |
| L62LF | 2450 | 28 | — |
| L62D | 2450 | 35 | — |
| L63 | 2650 | 34 | — |
| L64 | 2900 | 58 | — |
| P65 | 3500 | 82 | 29.5 |
| F68 | 8350 | >100 | 50 |
| F68LF | 7700 | 32 | 47 |
| L72 | 2850 | 25 | — |
| P75 | 4150 | 82 | 34 |
| F77 | 6500 | >100 | 48 |
| L81 | 2750 | 20 | — |
| P84 | 4200 | 74 | 34 |
| P85 | 4600 | 85 | 40 |
| P87 | 7850 | >100 | 49 |
| F88 | 10,800 | >100 | 55 |
| F92 | 3500 | 26 | — |
| P94 | 4600 | 76 | 38 |
| F98 | 13,500 | >100 | 56 |
| L101 | 3800 | 15 | — |
| P103 | 4900 | 86 | 30 |
| P104 | 5800 | 81 | 37.5 |
| P105 | 6350 | 91 | 42 |
| F108 | 15,500 | >100 | 57 |
| L121 | 4500 | 14 | — |
| L122 | 4900 | 19 | — |
| P123 | 5650 | 90 | — |
| F127 | 11,500 | >100 | 56 |

*in 1% aqueous solution

L—Liquid
P—Paste
F—Flakeable Solid
> = greater than